United States Patent [19]

Burke et al.

[11] Patent Number: 5,438,605
[45] Date of Patent: Aug. 1, 1995

[54] RING TUBE X-RAY SOURCE WITH ACTIVE VACUUM PUMPING

[75] Inventors: James E. Burke, Villa Park; Lester Miller, Forest Park, both of Ill.

[73] Assignee: Picker International, Inc., Highland Hts., Ohio

[21] Appl. No.: 163,148

[22] Filed: Dec. 6, 1993

Related U.S. Application Data

[63] Continuation-in-part of Ser. No. 862,805, Apr. 3, 1992, Pat. No. 5,268,955, and a continuation-in-part of Ser. No. 863,182, Apr. 3, 1992, Pat. No. 5,305,363, which is a continuation-in-part of Ser. No. 817,294, Jan. 6, 1992, Pat. No. 5,241,577, which is a continuation-in-part of Ser. No. 817,295, Jan. 6, 1992, Pat. No. 5,200,985, which is a continuation-in-part of Ser. No. 817,296, Jan. 6, 1992, abandoned.

[51] Int. Cl.$^6$ .............................................. H01J 35/04
[52] U.S. Cl. .................................. 378/135; 378/123; 378/141
[58] Field of Search ............. 378/4, 10, 11, 12, 15, 378/101, 121, 123, 130, 131, 132, 134, 135, 137, 141, 147, 136

[56] References Cited

U.S. PATENT DOCUMENTS

| | | | |
|---|---|---|---|
| 3,885,179 | 5/1975 | Friedel | 378/136 |
| 4,048,496 | 9/1977 | Albert | 250/272 |
| 4,122,346 | 10/1978 | Enge | 250/398 |
| 4,128,781 | 12/1978 | Flisikowski et al. | 378/135 |
| 4,135,095 | 1/1979 | Watanabe | 250/445 T |
| 4,203,036 | 5/1980 | Tschunt | 250/445 T |
| 4,227,088 | 10/1980 | Maydan et al. | 250/445 T |
| 4,274,005 | 6/1981 | Yamamura et al. | 250/445 T |
| 4,300,051 | 11/1981 | Little | 250/445 T |
| 4,368,535 | 1/1983 | Baumann | 378/15 |
| 4,417,171 | 11/1983 | Schmitmann | 313/16 |
| 4,501,566 | 2/1985 | Carlson et al. | 378/125 X |
| 4,521,900 | 6/1985 | Rand | 378/137 |
| 4,521,901 | 6/1985 | Rand | 378/138 |
| 4,531,226 | 7/1985 | Peschmann | 378/143 |
| 4,535,243 | 8/1985 | Peschmann | 250/363 S |
| 4,573,179 | 2/1986 | Rutt | 378/10 |
| 4,610,021 | 9/1986 | Peschmann et al. | 378/150 |
| 4,618,970 | 10/1986 | Rand et al. | 378/10 |
| 4,625,150 | 11/1986 | Rand | 315/111.3 |
| 4,631,741 | 12/1986 | Rand et al. | 378/10 |
| 4,644,168 | 2/1987 | Rand et al. | 250/398 |
| 4,821,305 | 4/1989 | Anderson | 378/136 |
| 4,866,745 | 9/1989 | Akai | 378/9 |
| 4,942,597 | 7/1990 | Van Acker et al. | 378/197 |
| 5,046,186 | 9/1991 | Rohmfeld | 378/125 |
| 5,067,143 | 11/1991 | Watanabe et al. | 378/110 |
| 5,125,012 | 6/1992 | Schittenhelm | 378/10 |
| 5,179,583 | 1/1993 | Oikawa | 378/135 |
| 5,191,600 | 3/1993 | Vincent | 378/10 |
| 5,268,955 | 12/1993 | Burke et al. | 378/135 |

FOREIGN PATENT DOCUMENTS

| | | |
|---|---|---|
| 3226950A | 1/1990 | Japan . |
| 377534A1 | 7/1990 | European Pat. Off. . |
| 455177A2 | 11/1991 | European Pat. Off. . |
| 456114A3 | 11/1991 | European Pat. Off. . |
| 2729353A | 1/1979 | Germany . |
| 1635090A1 | 7/1991 | U.S.S.R. . |

OTHER PUBLICATIONS

"A New Design For High Speed Computerized Tomography", Maydan, et al., IEEE Trans. on Nuclear Science, Vo. NS-26, No. 2, Apr. 1979, pp. 2870–2871.
"Brushless D.C. Motors and Servo Amplifiers", Inland Motor Advertisement, 1988 IM5MWPTT189, p. 21.

Primary Examiner—David P. Porta
Attorney, Agent, or Firm—Fay, Sharpe, Beall, Fagan, Minnich & McKee

[57] ABSTRACT

A toroidal x-ray tube housing (A) is composed of multiple sections which are clamped together and sealed by elastomeric gaskets (128). An annular anode (B) is mounted to the housing with coolant passages (12, 14) extending thereadjacent. A rotor (30) is rotated within the toroidal housing by a motor (60). At least one cathode assembly (C) is mounted to the rotor adjacent the anode. The rotor is supported by magnetic bearings (40) whose active coils are separated from the vacuum region by a magnetic window (48). Alternately, a series of vanes (136, 138) are provided to divide the vacuum chamber into a high vacuum region (132) adjacent the cathode and anode and a low vacuum region (134) adjacent the motor (60) and bearings (40, 150, 152) for rotatably supporting the rotor within the housing. An active vacuum pump, preferably a ion pump (112) and a getter (114) are hermetically sealed into the vacuum region for maintaining the vacuum.

27 Claims, 7 Drawing Sheets

RING TUBE X-RAY SOURCE WITH ACTIVE VACUUM PUMPING

This application is a continuation-in-part of U.S. application Ser. No. 07/862,805, filed Apr. 3, 1992, now U.S. Pat. No. 5,268,955 and U.S. application Ser. No. 07/863,182 now U.S. Pat. No. 5,305,363, also filed Apr. 3, 1992, which, in turn, are continuations-in-part of U.S. application Ser. Nos. 07/817,294 (now U.S. Pat. No. 5,241,577); 07/817,295 (now U.S. Pat. No. 5,200,985); and 07/817,296 (now abandoned), all filed on Jan. 6, 1992.

BACKGROUND OF THE INVENTION

The present invention pertains to the art of x or gamma ray generation. It finds particular application in conjunction with x-ray tubes for CT scanners and will be described with particular reference thereto. However, it is to be appreciated, that the present invention will find application in conjunction with the generation of radiation for other applications.

Typically, a patient is positioned in a prone position on a horizontal couch through a central bore of a CT scanner. An x-ray tube is mounted on a rotatable gantry portion and rotated around the patient at a high rate of speed. For faster scans, the x-ray tube is rotated more quickly. However, rotating the x-ray more quickly decreases the net radiation per image. As CT scanners have become quicker, larger x-ray tubes which generate more radiation per unit time have been required, which, of course, cause high inertial forces.

High performance x-ray tubes for CT scanners and the like commonly include a stationary cathode and a rotating anode disk, both enclosed within an evacuated housing. As stronger x-ray beams are generated, there is more heating of the anode disk. In order to provide sufficient time for the anode disk to cool by radiating heat through the vacuum to surrounding fluids, x-ray tubes with progressively larger anode disks have been built.

The larger anode disk requires a larger x-ray tube which does not readily fit in the small confined space of an existing CT scanner gantry. Particularly in a fourth generation scanner, incorporating a larger x-ray tube and heavier duty support structure requires moving the radiation detectors to a larger diameter. This requires more detectors for the same resolution and provides a longer path length between the x-ray tube and the detectors. The longer path length can cause more radiation divergence and other degradation of the image data. Not only is a larger x-ray tube required, larger heat exchange structures are required to remove the larger amount of heat which is generated.

Rather than rotating a single x-ray tube around the subject, others have proposed using a switchable array of x-ray tubes, e.g. five or six x-ray tubes in a ring around the subject. See, for example, U.S. Pat. No. 4,274,005 to Yamamura. However, unless the tubes rotate only limited data is generated and only limited image resolution is achieved. If multiple x-ray tubes are rotated, similar mechanical problems are encountered trying to move all the tubes quickly and remove all of the heat.

Still others have proposed constructing an essentially bell-shaped, evacuated x-ray tube envelope with a mouth that is sufficiently large that the patient can be received a limited distance in the well of the tube. See, for example, U.S. Pat. No. 4,122,346 issued Oct. 24, 1978 to Enge or U.S. Pat. No. 4,135,095 issued Jan. 16, 1979 to Watanabe. An x-ray beam source is disposed at the apex of the bell to generate an electron beam which impinges on an anode ring at the mouth to the bell. Electronics are provided for scanning the x-ray beam around the evacuated bell-shaped envelope. One problem with this design is that it is only capable of scanning about 270°. Another problem is that the very large evacuated space required for containing the scanning electron beam is difficult to maintain in an evacuated state. Troublesome and complex vacuum pumping systems are required. Another problem is that no provision can be made for off-focus radiation. Another problem resides in its large physical size.

Still others have proposed open bore x-ray tubes. See, for example, U.S. Pat. No. 5,125,012 issued Jun. 23, 1992 to Schittenhelm and U.S. Pat. No. 5,179,583 issued Jan. 12, 1993 to Oikawa. These large diameter tubes are constructed analogous to conventional x-ray tubes with a glass housing and a sealed vacuum chamber. Such tubes are expensive to fabricate and are susceptible to repair in case of tube failure. Moreover, maintaining the vacuum within the tubes was tenuous due to the large surface area within the vacuum that can outgas contaminants into the vacuum area as well as the inclusion of components such as bearings, which tend to contaminate the vacuum.

Others have suggested the use of active vacuum pumping when the evacuated area was large. See, for example, U.S. Pat. No. 4,227,088 issued Oct. 7, 1980 to Mayden, et al. and U.S. Pat. No. 4,003,051 issued Nov. 10, 1981 to Little. The Mayden and Little structures had several drawbacks such as limitations on axial receipt of the patient and mechanical bearings and structures within the vacuum. For high speed rotation, mechanical bearings would require lubrication. One problem which these patents fail to address adequately is the difficulty of maintaining a high, $10^{-6}$ Torr vacuum for x-ray generation in a chamber which contains lubricants or epoxies. Conversely, there is also a problem maintaining sufficient lubrication on bearings which are disposed in high vacuums.

The present invention contemplates a new and improved x-ray tube which can provide a tenfold or better power increase over currently available rotating anode x-ray tubes.

SUMMARY OF THE INVENTION

In accordance with one aspect of the present invention, a large diameter, tubular evacuated housing is provided. An anode target is disposed in the housing with an annular window for directing x-rays toward a central axis of the annular housing. A path is defined in thermal communication with the anode for receiving a cooling fluid. An annular rotor is rotatably received in the toroidal housing. A cathode is mounted on the rotor for generating an electron beam which strikes the target anode. A means is provided for rotating the rotor such that the electron beam is rotated around the anode. An active vacuum pump is connected with the housing to maintain a vacuum of at least $10^{-6}$ Torr therein.

In accordance with one embodiment, the active vacuum pump includes an internal ion pump hermetically sealed within the housing.

In accordance with another more limited aspect of the present invention, a getter is also disposed within the housing.

In accordance with another aspect of the present invention, means are provided for maintaining at least a higher vacuum level within one region of the housing interior and a lower vacuum level in another region of the housing interior.

In accordance with a more limited aspect of the present invention, a high vacuum level is maintained between the cathode and anode and a lower vacuum level is maintained adjacent the means for rotating the electron beam around the anode.

In accordance with a yet more limited aspect of the present invention, the means for rotating the electron beam includes mechanical motor windings, mechanical bearings, electromagnets, or other structures that contain polymers such as lubricants or epoxies that are incompatible with high vacuums are disposed in the lower vacuum region.

In accordance with another aspect of the present invention, the housing is constructed of multiple parts interconnected together with elastomeric seals.

In accordance with a more limited aspect of the present invention, intermeshing vanes are connected with the rotor and housing to maintain the vacuum differential between the higher and lower vacuum region.

In accordance with another more limited aspect of the present invention, means are provided for condensing vapors of the polymers in the lower vacuum region.

In accordance with another aspect of the present invention, the cathode is maintained at a potential of at least −100 keV relative to the rotor. The rotor and housing are preferably maintained substantially at ground potential.

In accordance with another aspect of the present invention, a box collimator is mounted to the rotor. A first pair of walls define beam thickness and a second pair define fan beam angle.

In accordance with another aspect of the present invention, a pair of coiling passages are defined along the anode for more uniform anode cooling.

One advantage of the present invention is that it increases the power over conventionally available 125 mm and 175 mm anode x-ray tubes.

Another advantage of the present invention is that it provides for efficient cooling of the anode.

Another advantage of the present invention is that it facilitates higher speed scans.

Another advantage of the present invention resides in its low bearing wear and long tube life.

Another advantage of the present invention is that the tube is field repairable.

Another advantage of the present invention is that it actively maintains a high vacuum between the cathode and anode.

Another advantage of the present invention is that it is amendable to the placement of components within the vacuum chamber which are incompatible with the high vacuums normally maintained adjacent the cathode and anode.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIGURE i is a cross-sectional view of a toroidal, rotating cathode x-ray tube in accordance with the present invention.

DETAILED DESCRIPTION OF THE PREFERRED EMBODIMENTS

Figure 1:
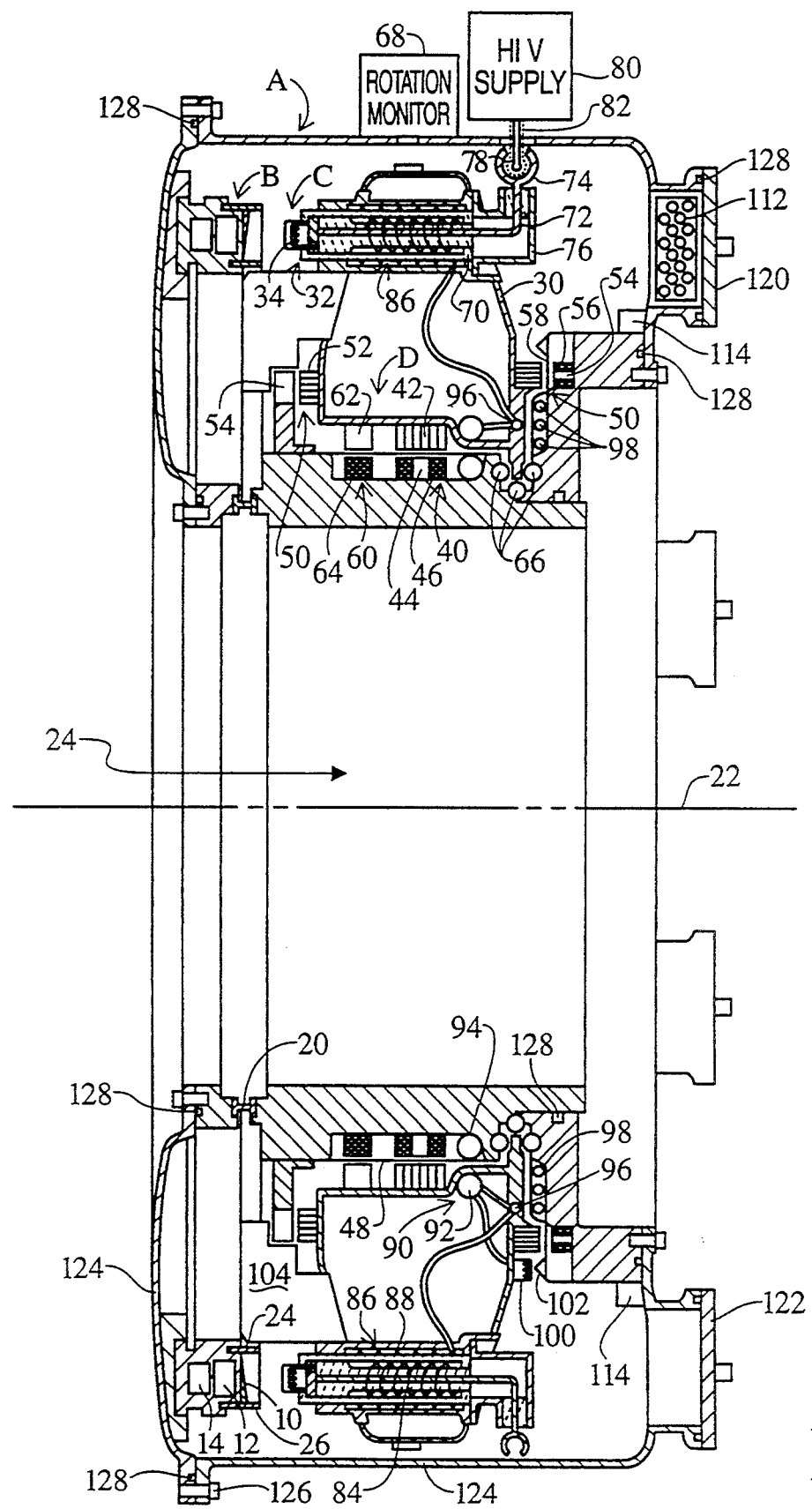

With reference to FIG. 1, a toroidal housing A defines a large, generally donut-shaped interior volume. An anode B is mounted within the toroidal housing interior volume and extends circumferentially therearound. A cathode means C is disposed within the toroidal housing interior space for generating at least one beam of electrons. A means D selectively rotates the electron beam around the anode B.

More specifically, the anode B is a tungsten disk having a tungsten face 10 upon which the electron beam impinges. The anode assembly defines an annular anode adjacent cooling fluid path or channel 12 in intimate thermal communication with the anode face, specifically along an opposite surface of the anode. Optionally, the anode can have internal passages, fins, and the like to promote thermal communication with the cooling fluid. A fluid circulating means circulates cooling fluid into an outer passage 14 of the fluid cooling path about 360° around then back through an anode adjacent fluid passage 12 back through another 360°. The dual flow-passage portions in opposite directions help maintain a more uniform anode temperature. The fluid circulating means circulates the hot fluid from the anode adjacent portion 12 of the through a heat exchanger and returns cooled fluid to the outer portion 4.

A window means 20 is mounted in the housing A in radial alignment with the tungsten face 0 of the target anode. The window is positioned such that x-rays generated by interaction of the electron beam and the tungsten target anode are directed transverse to a central axis 22 of a bore 24 of the toroidal tube.

An annular ring or rotor 30 Which extends around an interior of the toroidal housing A. The rotor includes a plurality of bores, e.g. a half dozen, for receiving a corresponding plurality of cathode assemblies C. Each of the cathode assemblies includes a cathode cup 32 which contains a filament or other electron source 34. The filament and the anode are maintained at a high relative voltage relative to each other, e.g. 200 keV. The housing A and the rotor 30 are maintained at the same potential, preferably ground potential. In the preferred embodiment, the anode is also maintained at ground potential and the cathode cup is insulated from the rotor 30 and maintained at about −200 keV. Alternately, the material within which the fluid path 12 is defined may be constructed of an electrical insulator and the anode is maintained at approximately +100 keV and the cathode is maintained at about −100 keV relative to ground.

The rotor 30 is rotatably supported within the housing A on a bearing means 40, a magnetic levitation bearing in the embodiment of FIG. 1. The magnetic levitation bearing includes rings of silicon steel 42, which are stable within the vacuum, mounted along an inner radius of the rotor 30. Passive and active elements including permanent magnets 44 and electromagnets 46 are disposed closely adjacent the rings 42 of silicon iron but outside of the vacuum region. The housing A includes a magnetic window 48 which separates the vacuum region from the electromagnets 46. The magnetic window permits magnetic flux to pass but prevents epoxy or other polymers commonly used in coils from outgassing into the vacuum region.

To maintain the alignment of the rotor ring 30, a pair of oppositely disposed magnetic levitation bearings 50 are mounted on opposite sides of the rotor. Each has rings of silicon steel 52 and permanent magnets 54 to provide opposing forces on the rotor. The magnetic levitation bearing on one side also has electromagnetic coils 56 to adjust the relative opposing forces. Position sensors, not shown but conventional in the art, are provided for controlling the electromagnetic coils to maintain the position of the rotor precisely. The electromagnetic coils 56 are again separated from the vacuum region of the housing by a magnetic window 58.

A brushless, large diameter inductor motor 6 includes a rotor 62, preferably of permanent magnets, mounted to the rotor 3 within the vacuum region. A stator 64 including electromagnetic windings, is positioned directly opposite the rotor 62 but across the magnetic window 48 outside of the vacuum region. Mechanical roller bearings 66, normally out of contact with the rotor, are provided to support the rotor 30 in the event the magnetic levitation system should fail. The mechanical roller bearings prevent the rotor from interacting with the stationary housing A and other associated structures. An angular position monitor 68 monitors the angular position of the rotation of the rotor 30, hence the angular position of the cathode assemblies and the apices of the x-ray beams precisely.

Each of the cathode assemblies 32 include insulation 70 for insulating the cathode assembly from the rotor 30. An electrical conductor 72 extends through the insulation 7e from one end of the filament 34 to a toroidal ring 74. The toroidal ring 74 is supported by but insulated from the rotor 3e by a series of mounting brackets 76. A hot cathode filament 78 is connected with a high voltage supply system 80. Preferably, the high voltage supply 80 is of a compact, high frequency type that is directly attached to the hot cathode 78 to avoid the problems of high voltage cables and terminations. The hot voltage cathode filament 78 is preferably of a lowered function type. The toroidal channel 74 which partially surrounds the hot cathode filament 78 is maintained at the potential of the hot filament by the transfer of electrons therebetween. Preferably, a grid 82 is disposed around the filament for grid control, current regulation, and active filtering.

The other end of the filament 34 is connected with a secondary coil 84 of an isolation coil 86 which is supported on the insulating material 70. A primary coil 88 is separated from the secondary coil 84 by the insulation 70. The filament is connected with one end of the secondary coil and the other end of the secondary coil is connected with the other end of the filament coil by the lead 72. One end of the primary coil is connected to the rotor, i.e. ground, and the other is connected to a filament current source 90. In the preferred embodiment, the filament current source includes a secondary transformer winding 92 mounted to the rotor 3e and connected with the primary winding 88. A primary transformer winding 94 is disposed across the magnetic window 48 from the secondary winding. For controlling which of the cathode assemblies are generating x-rays, the secondary coil is connected to a series of reed switches 96. The reed switches are controlled by electromagnets 98 disposed on the housing. By selectively applying current the electromagnets 98, the reed switches are selectively opened and closed to control which cathode assemblies are receiving filament currents.

To assure that the rotor 30 is maintained at ground, the secondary transformer coil 92 is also connected with a filament 100. The filament 100 is heated to boil off electrons to create a current path to a collector ring 102 on the housing. This current flow maintains the rotor 30 at the same potential as the housing A.

The rotor also carries a collimator means, preferably a box collimator 104. Opposite side walls of the collimator box 104 in a direction parallel to the central axis control the width or thickness of the x-ray beam. Oppositely disposed walls of the collimator box e4 in the transverse direction control the fan angle of the xray beam. The collimator assembly also blocks any scattered x-rays from merging with the x-ray beam.

To maintain the vacuum within the vacuum region of the housing A, an active vacuum pumping means is provided. In the preferred embodiment, the active vacuum pumping means includes an ion pump which is mounted and sealed within the vacuum region of the housing. Because an ion pump uses high electrical potential to embed molecules from the vacuum region into a collector plate, no external connections, other than electrical connections, are necessary. A getter 114, i.e. a material which absorbs ions from the vacuum region, is also mounted inside of the housing A. Alternately, other types of vacuum pumps which maintain a vacuum of about $10^{-6}$ Torr or lower may be utilized. For example, cryogenic vacuum pumps may be utilized. If a cryogenic pump is provided, an uninterruptible power supply is preferable for maintaining operation of the cryogenic vacuum pump. If an uninterruptible power supply is not utilized, a significant duration can be required to bring the cryogenic vacuum pump back down to temperature after a momentary power interruption. Turbomolecular pumps are also contemplated. However, an uninterruptible power supply is still highly advantageous with a turbo-molecular pump to eliminate significant downtime after a power outage. Diffusion pumps which are silent and cost-effective are also contemplated. If a diffusion pump is used, a mechanical back-up pump is also provided. The mechanical back-up pump may be externally vented, particularly if an oil pump is used. To eliminate the oil vapor problems, a simple dry stage of compression such as a roots blower can be utilized. This same combination may be used with a turbo-molecular pump as well.

The housing A includes a removable panel portion 120 which provides access to the ion pump 112 and the getter 114 to enable their periodic replacement. Preferably, a portable vacuum pump is connected temporarily to another housing port 122 after the housing is opened to redraw the vacuum quickly. The housing includes a plurality of housing portions 124 which are interconnected by simple bolts or compression fittings 126. Elastomeric gaskets 128 seal the vacuum region from the exterior. Due to the active vacuum pumping, outgassing from elastomeric seals, welds, and the like can be readily accommodated.

Figure 2:
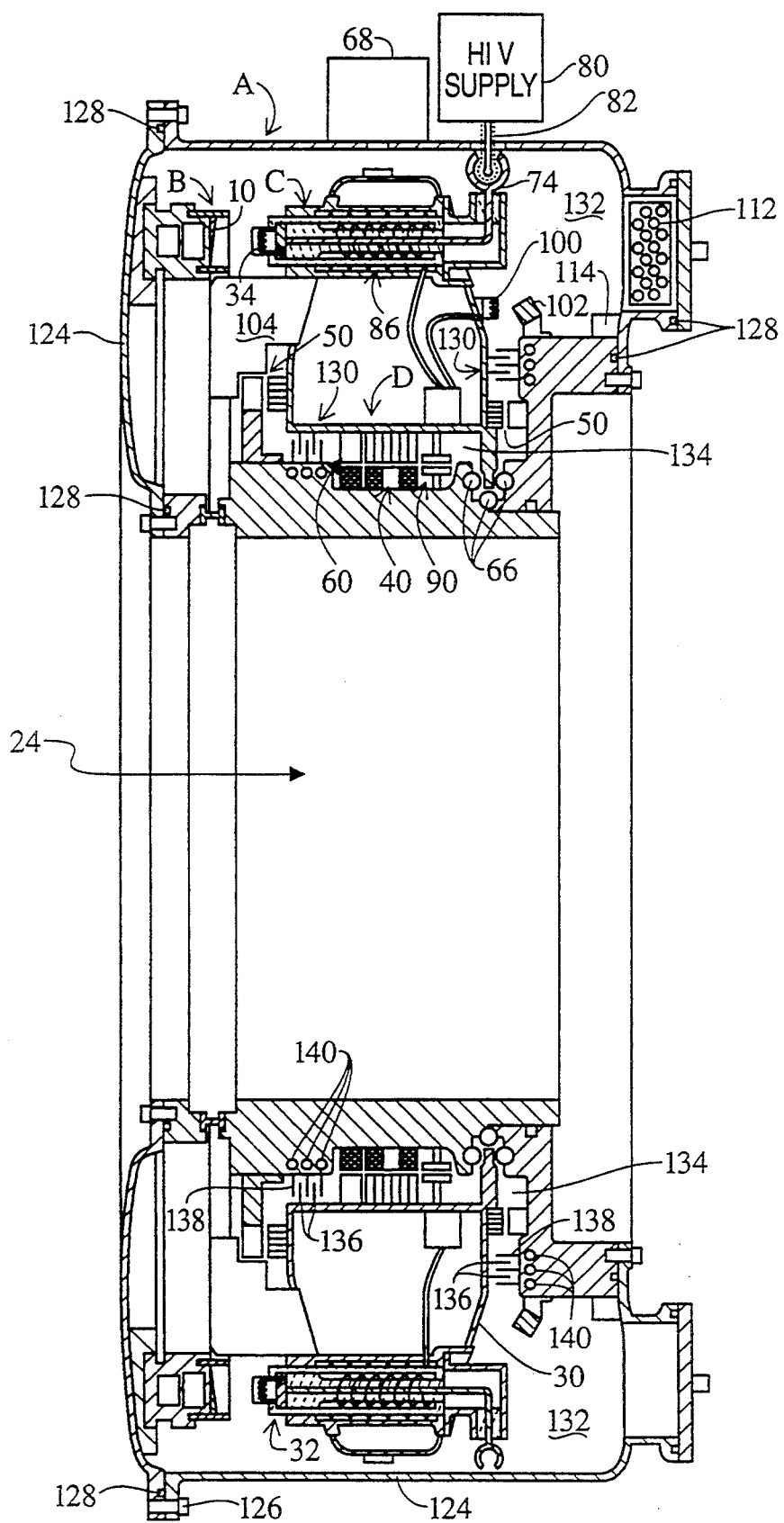
FIG. 2 is a transverse cross-sectional view of an alternate embodiment of the toroidal x-ray tube of FIG. 1.

In the embodiment of FIG. 2, like components are denoted by the same reference numerals as FIG. 1. The primary difference between the embodiments of FIG. 1 and 2 is that the active portions 46, 56 of the magnetic bearings 40, 5 and the stator 64 of the drive motor 6 are disposed within the vacuum region. To reduce the outgassing problems normally associated with the epoxy potting and other polymeric materials commonly found in electrical windings, means 130 are provided for dividing the vacuum region into a high vacuum region 132 and a low vacuum region 134. More specifically, the means 130 permits the travel of light gases, but blocks or at least resists the flow of hydrocarbons such that the partial pressure of hydrocarbons is higher in region 134. In the preferred embodiment, the means 130 is a molecular drag means which provides for limited vacuum communication between the low vacuum region around the magnetic bearings 40, 50 and motor 60 and the portions of the vacuum region adjacent the cathode and anode. In the preferred embodiment, a series of vanes 136 are mounted to the rotor and another series of intermeshing vanes 138 are mounted to the housing. A second set of the vanes 136 and 138 are disposed at the opposite extreme of the lower vacuum region. Cooling passages 140 are disposed closely adjacent the vanes on the housing side to cool the vanes sufficiently that outgassed hydrocarbons and polymers from the lower vacuum region adhere o the vanes. Ice water cooling is normally sufficient to condense the hydrocarbon vapors. Closely intermeshed shield vanes can create a pressure differential thereacross such that the main higher vacuum region is maintained at least at $10^{-6}$ Torr while the lower vacuum region is maintained at about $10^{-4}$ Torr. The partial pressure of light gases, such as oxygen, is the same in both regions, but the vapor pressure of heavy vapors, such as hydrocarbons, greases, etc. is higher in the low vacuum region. The lower vacuum draws less hydrocarbon vapor into the vacuum.

In the embodiment of FIG. 2, the filament current source 90 includes inductive or capacitive electrical potential transfer rings. The transferred electrical potential is encoded, e.g. with higher and lower voltage pulses, for a switching circuit 42. The switching circuit decodes the signal and controls the cathode assemblies C accordingly.

Figure 3:
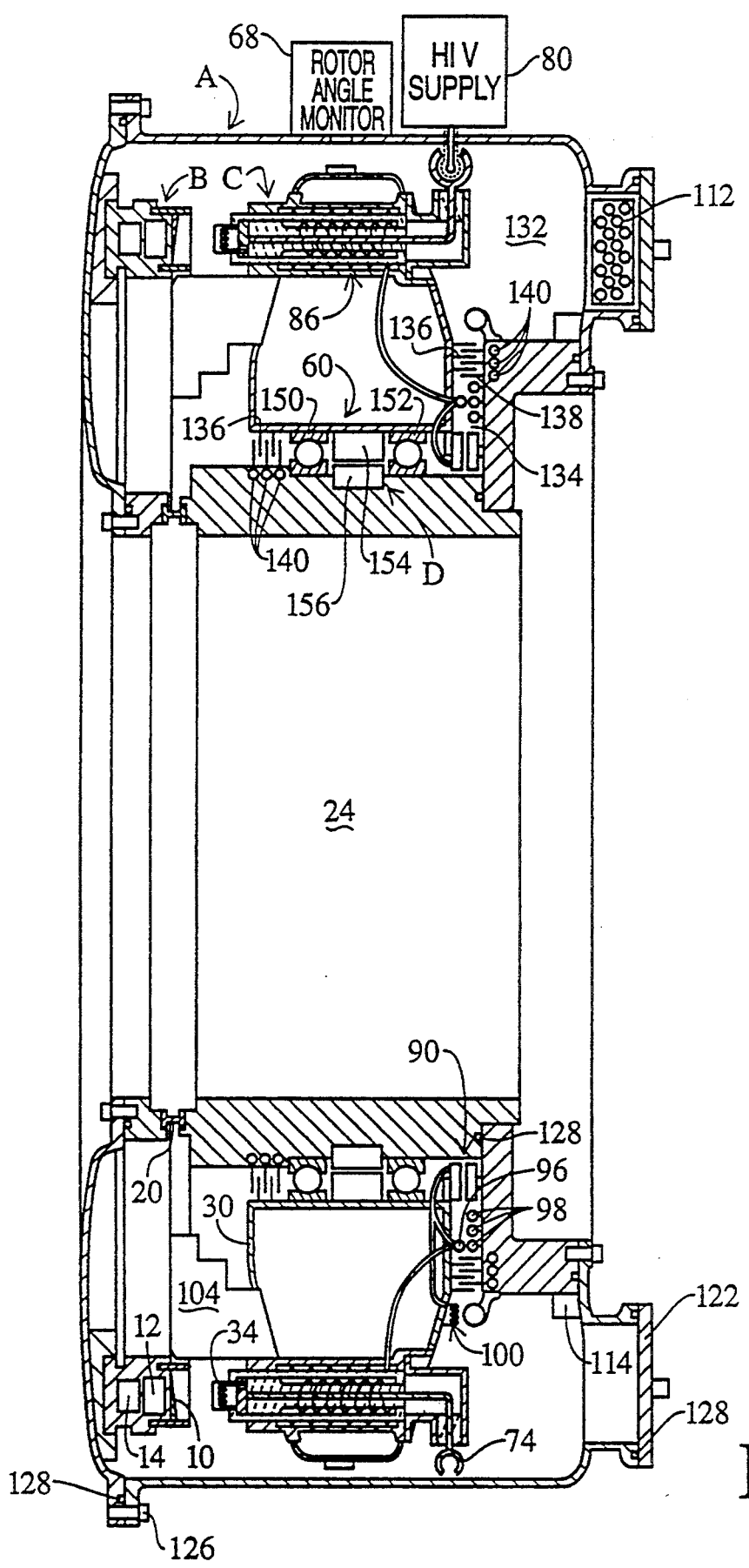
FIG. 3 is a transverse cross-sectional view of another alternate embodiment of the toroidal x-ray tube of FIG. 1.

With reference to FIG. 3 in which like elements of FIGS. 1 and 2 again carry the same reference numerals, more conventional mechanical components are able to be utilized due to the multiple vacuum levels. More specifically, the rotor 30 is mounted on bearings 150, 152. Because the vacuum differential maintaining means 130 maintain a vacuum of $10^{-4}$ Torr or less, lubricants, epoxies, and other materials which are not suited for use in $10^{-6}$ vacuums can be and are utilized. Although mechanical roller bearings are illustrated, journal bearings, foil bearings, hydrodynamic bearings and the like are also contemplated. A conventional motor 60 has both its rotor 154 and stator 156 disposed in the lower vacuum region 134, one attached to the rotor 30 and the other attached to the housing A.

Figure 4:
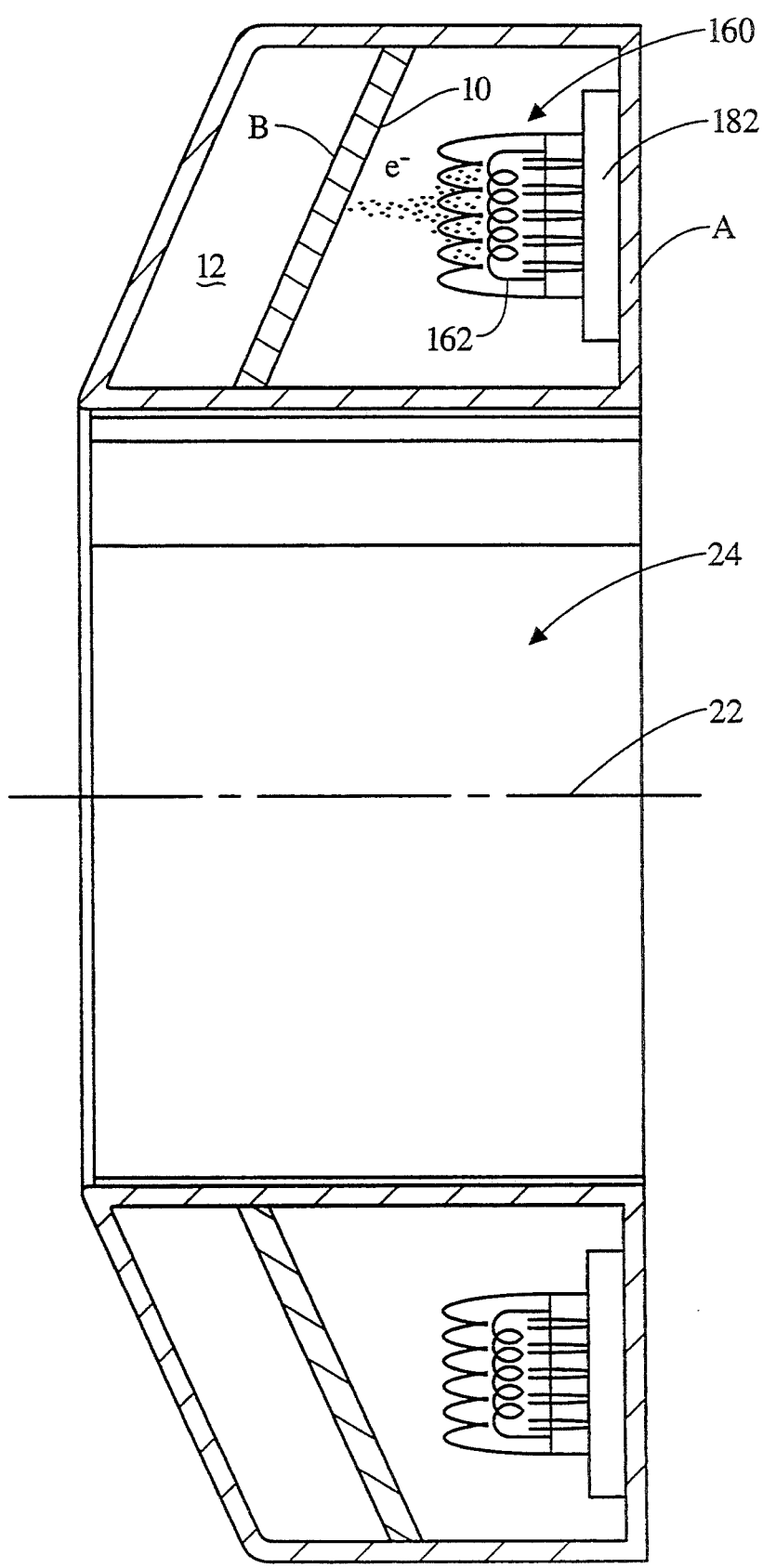
FIG. 4 is a transverse sectional view of an alternate embodiment of the toroidal x-ray tube of FIGURE 1.
Figure 5:
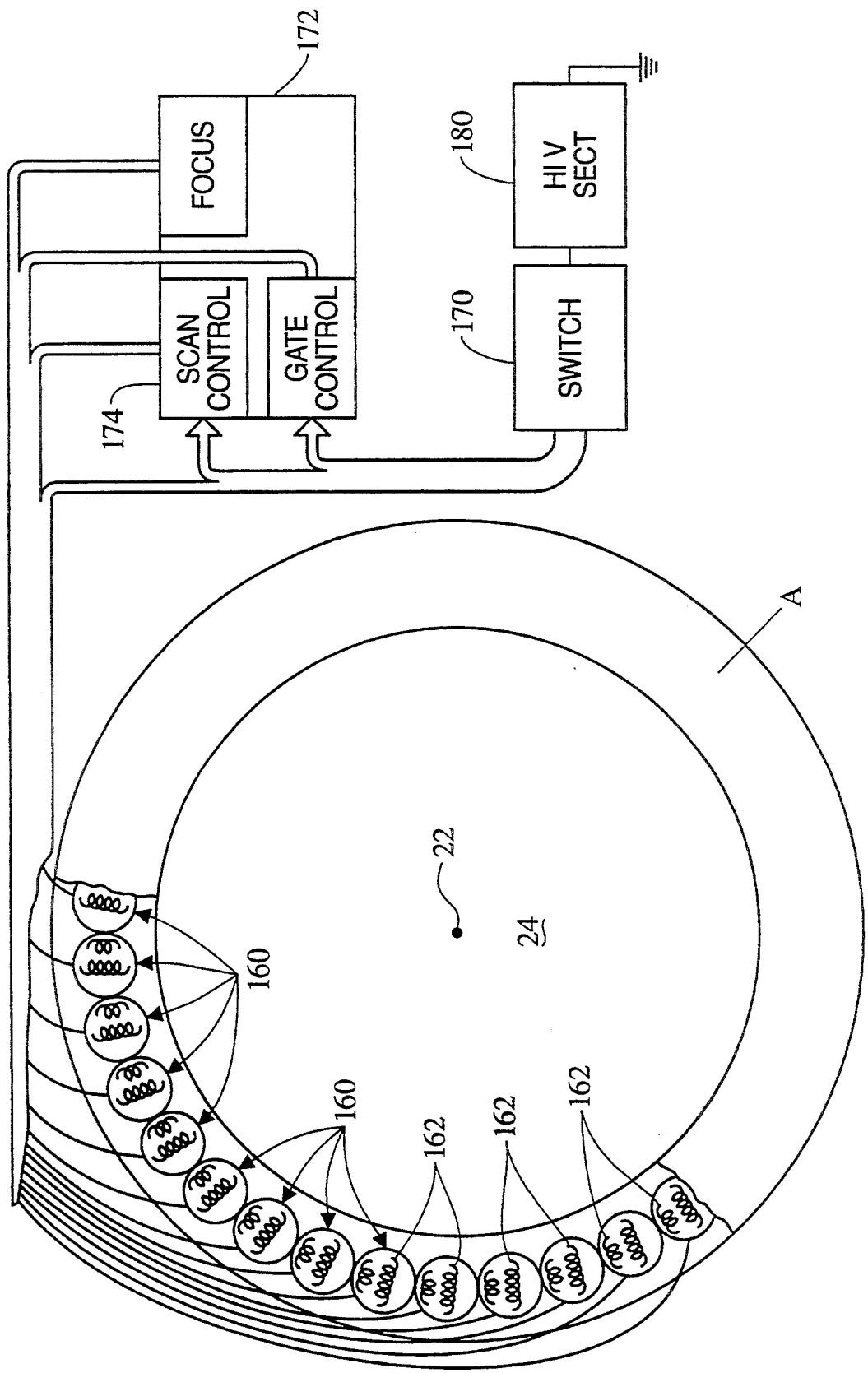
FIG. 5 is a front view in partial section of the tube of FIG. 4.
Figure 6:
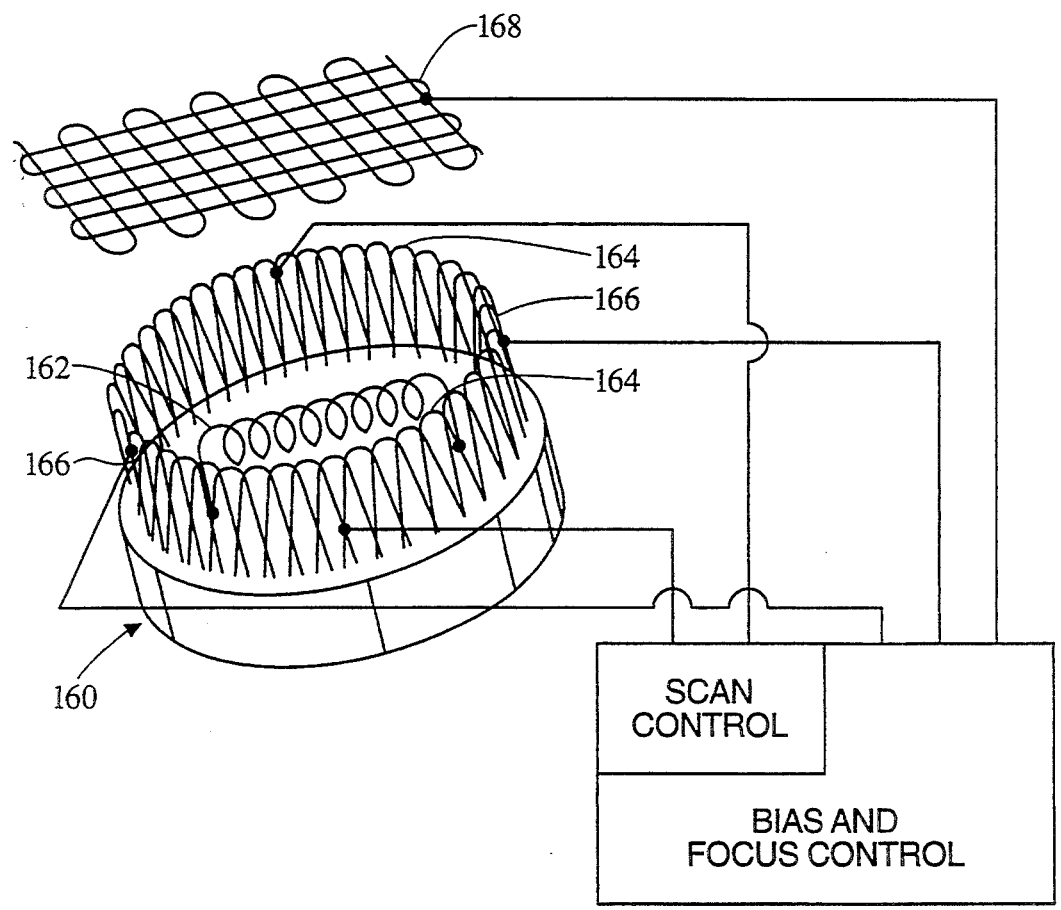
FIG. 6 is a perspective view of one of the cathode cups of FIGS. 4 and 5.

In the embodiment of FIGS. 4, 5, and 6, the housing A is again toroidal. The anode B is again annular and defines a cooling path 12 with a portion of the housing. The tungsten anode face 10 is disposed toward the cathode assembly C to generate the x-ray beam when excited by an electron beam from the cathode. The cathode assembly includes a multiplicity of cathode cups 160 arranged closely adjacent to each other in a ring around the housing. Each cathode cup includes a cathode filament 2 which is heated by an excitation current to undergo thermionic emission. A grid assembly includes a pair of grids 164 for focusing the generated electron beam in a circumferential direction relative to the anode and a pair of grids 166 for focusing the electron beam in a radial direction. A gate electrode 168 selectively permits and prevents the electron beam from reaching the anode. In the preferred embodiment, a switching means 170 sequentially switches each of the gate grids 168 to permit the passage of electrons. In this manner, the electron beam is stepped, or moved in other selected patterns, around the anode.

A biasing and focusing control circuit 172 applies appropriate bias voltages to the grid pairs 164, 166 to focus the electron beam at a selected point on the anode relative to the cathode cup with a selected beam dimension. Optionally, the biasing and focusing circuit control 172 may include a scanning means 174 for gradually or incrementally shifting the bias voltage between the grids 164, 166 to sweep or scan the electron beam continuously or in a plurality of steps to a plurality of positions along an arc segment of the anode commensurate with a circumferential length of the cathode cup. Each time the switching means 170 switches to the next cathode cup, it causes the beam scanning means 174 to sweep the electron beam along each of its preselected circumferential beam positions.

A high voltage means 180 biases the cathode assembly C to a high voltage relative to the housing. A ceramic insulation layer 182 insulates the cathode cups from the housing such that the cathode cups can be maintained at a potential, on the order of $-100$ keV, relative to the housing. For operator safety, the housing is preferably held to ground and the cathode cups are biased on the order of $-100$ keV relative to the housing and the anode. Alternately, the anode may be electrically insulated from the housing and biased to a positive voltage relative to the housing. In such an embodiment, care must be taken that the cooling fluid is dielectric such that the cooling fluid does not short the anode to the housing.

The filaments of all the cathode cups are preferably driven concurrently. The switching means 170 further switches the high voltage supply 180 sequentially to each of the cathode cups 160. In this manner, only one or a small group of cathode cups at time is maintained at a sufficiently high voltage relative to the anode to cause an x-ray beam and the generation of x-rays. Of course, either the grid 168 or the individual cathode cup biasing (but not both) may be used to control the electron and x-ray beams.

Each individual cathode segment or cup preferably is constructed with radial slots with series or parallel connected filaments in each slot. Such slot and filament portions naturally provide line focus electron beams desirable for target loading when the grid voltage is removed from the desired segment. This radially slotted section may be divided in half and appropriately insulated to facilitate sweeping the focal spot across the anode track. These halves can also be used to alter the size of the focal spot.

An additional refinement may be obtained by heating the filament or, more generally the electron emitter by a second cathode structure behind the emitter and accelerated by a more modest potential and a locally controlled grid in a similar manner to the main cathode structure. One of the benefits achieved by this construction is that low temperature, low work function filaments may be employed. This lowers the heating current requirement substantially. The electron emitters can be heated very uniformly to achieve a very uniform focal spot. These emitters furthermore may be constructed of tungsten ribbon or other suitable shaped material of low effect thermal mass so that an emitter may be boosted to operating temperature very quickly, requiring only grid control of the second filament to achieve markedly lower heating energy to the electron emitter and a large increase in reliability.

Figure 7:
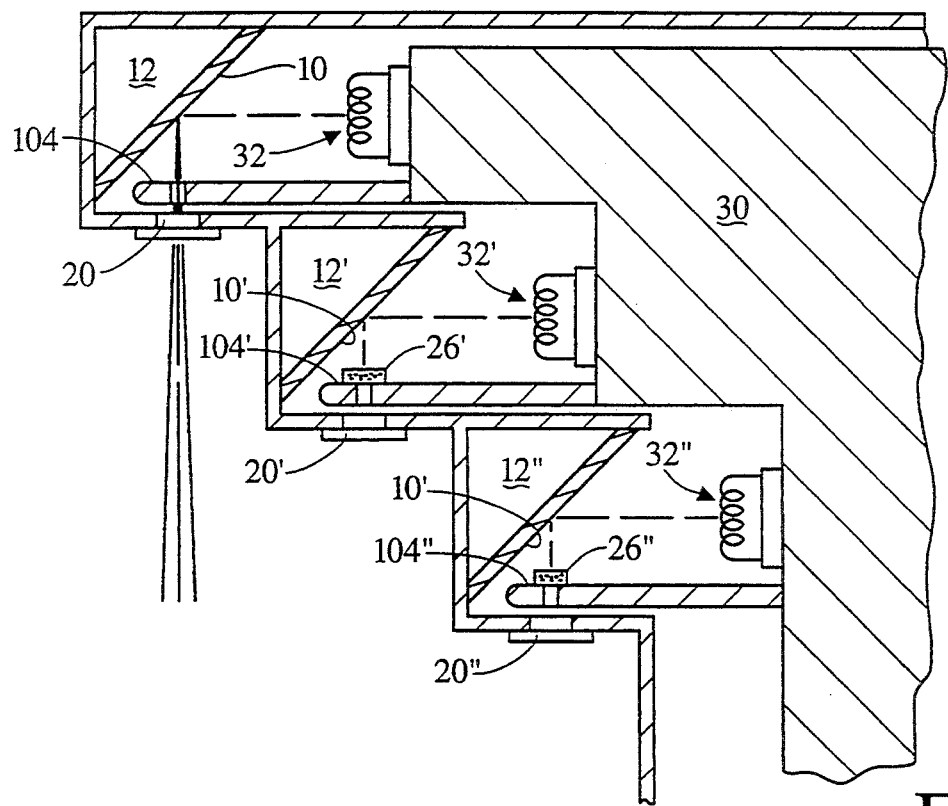
FIG. 7 is a sectional view of the anode/cathode cup portion of a multiple anode tube.
Figure 8:
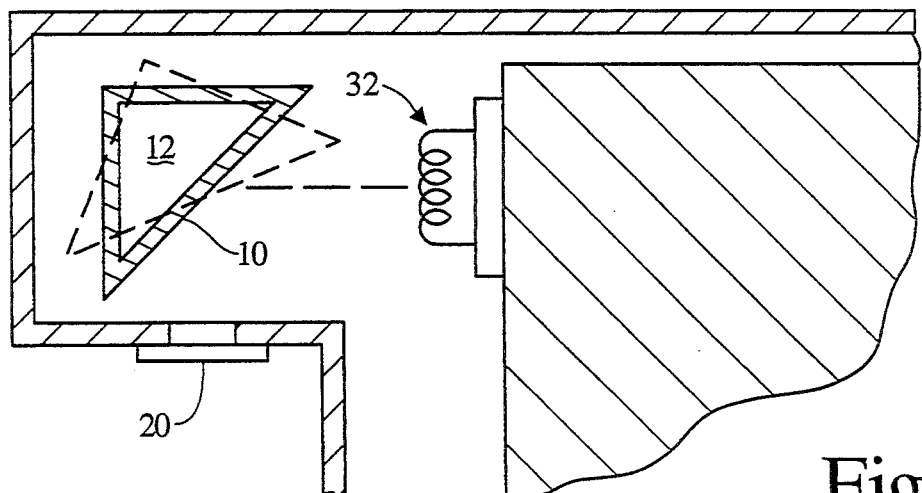
FIG. 8 is a sectional view of the anode/cathode cup portion of a movable anode tube.

With reference to FIG. 7, multiple anodes 10', and " are mounted in stair/step fashion, each adjacent a corresponding window 20, 20', and 20". A cathode cup 32, 32', and 32" are mounted to the annular ring 30. Preferably, the annular ring 30 is rotatably mounted on magnetic bearings as described above. Alternately, multiple cathode cups can be positioned around the annular ring 30 as described in conjunction with FIGS. 3-5 above. Each cathode cup is controlled by the magnetic switch control such that the operator can select among a plurality of modes of operation. For example, all three cathode cups can be operated simultaneously for multi-slice imaging. As another alternative, collimators 104, 104' and 104" can be associated with each of the anode/cathode cup combinations. Each collimator can have a different aperture size to produce a different size or shape x-ray beam. As another alternative, each anode/cathode cup combination can have a different filter or compensator 26'26", associated with it With reference to FIG. 8, the anode assembly has a face 10 which is movable relative to the electron source 32. In the embodiment illustrated in FIG. 8, the anode surface 10 along with the surrounding structure that defines the cooling fluid channel 12 is selectably rotatable or tippable as illustrated, to an exaggerated degree, in phantom. Instead of rotating, the surface may be flexed. Also, the anode surface may be other than a single plane such that shifting its position alters the characteristics of the anode surface which receives the electron beam.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An x-ray tube comprising:
a generally toroidal housing having an evacuated interior;
an annular anode surface mounted in the toroidal housing interior, the anode surface being in thermal communication with a circulated cooling fluid passage such that the cooling fluid removes heat from the anode surface, the fluid passage being divided into an inlet fluid passage extending substantially 360° around the x-ray tube, the inlet fluid passage being connected with an anode adjacent fluid passage disposed more closely adjacent the anode surface, the anode adjacent fluid passage being disposed between the inlet fluid passage and the anode surface and extending substantially 360° around the x-ray tube to an outlet, such that heat transfer between the inlet and anode adjacent fluid passages improves uniformity of cooling along the anode surface;
a rotor rotatably disposed within the housing interior;
at least one cathode mounted to the rotor for rotation therewith, the cathode emitting electrons to form an electron beam that strikes the anode surface to generate an x-ray beam, the electron beam being rotated round the anode surface as the rotor rotates within the housing;
an active vacuum pump connected to the housing interior for actively maintaining a vacuum of at least $10^4$ Torr therein.

2. An x-ray tube comprising:
a generally toroidal housing having an evacuated interior;
an annular anode surface mounted in the toroidal housing interior, the anode surface being in thermal communication with a circulated cooling fluid passage such that the cooling fluid removes heat from the anode surface;
an annular rotor rotatably disposed within the housing interior;
at least one cathode assembly mounted to the rotor for rotation therewith, the cathode assembly including a cathode for emitting electrons to form an electron beam that strikes the anode surface to generate an x-ray beam;
a means for rotating the annular rotor such that electron beam is rotated around the anode surface;
an active vacuum pump hermetically sealed into the housing interior with no exhaust for discharging atoms evacuated form the interior region, the active vacuum pump actively maintaining a vacuum of at least $10^{-6}$ Torr in the housing interior.

3. The x-ray tube as set forth in claim 1 wherein the active vacuum pump includes an ion pump which embeds atoms evacuated from the vacuum region into a collector.

4. The x-ray tube as set forth in claim 1 further including a getter, which chemically bonds atoms from a vacuum region, disposed in the interior of the toroidal housing.

5. An x-ray tube comprising:
a generally toroidal housing defining a vacuum region therein;
an annular anode surface mounted in the toroidal housing vacuum region, the anode surface being in thermal communication with a circulated cooling fluid passage such that the cooling fluid removes heat from the anode surface;
a rotor rotatably disposed within the vacuum region;
at least one magnetic levitation bearing supporting the rotatable anode, the magnetic levitation bearing including:
rings of a ferrous material mounted to the rotor along an inner diameter thereof within the vacuum region and a ring of permanent and electromagnetic coils disposed radially inward from and closely adjacent to the rings of ferrous material; and a magnetic window which seals at least the electromagnetic coils from the vacuum region while permitting magnetic fields therefrom to pass therethrough to interact with the ferrous rings;

at least one cathode assembly mounted to the rotor for rotation therewith, the cathode assembly emitting electrons to form an electron beam that strikes the anode surface to generate an x-ray beam, the electron beam being rotated around the anode surface as the rotor rotates within the vacuum region;

an active vacuum pump connected to the vacuum region for actively maintaining a vacuum of at least $10^{-6}$ Torr therein.

6. The x-ray tube as set forth in claim 5 wherein the active vacuum pumping means includes an ion pump hermetically and removably sealed into the housing.

7. An x-ray tube comprising:

a generally toroidal housing having an evacuated interior;

a means for dividing the interior of the toroidal housing into at least a higher vacuum region and a lower vacuum region;

an annular anode surface mounted in the toroidal housing interior higher vacuum region, the anode surface being in thermal communication with a circulated cooling fluid passage such that the cooling fluid removes heat from the anode surface;

a rotor rotatably disposed within the interior of the toroidal housing;

at least one cathode assembly mounted to the rotor for rotation therewith, the cathode assembly including a cathode for emitting electrons to form an electron beam that traverses the higher vacuum region and strikes the anode surface to generate an x-ray beam;

a means for rotating the annular rotor such that electron beam is rotated around the anode surface;

an active vacuum pump connected to the housing interior for actively maintaining a vacuum of at least $10^{-6}$ Torr in the higher vacuum region.

8. The x-ray tube as set forth in claim 7 wherein the anode surface and cathode are disposed in the higher vacuum region and at least a portion of the rotor is disposed in the low vacuum region.

9. The x-ray tube as set forth in claim 8 wherein the means for rotating the rotor includes a motor disposed in the lower vacuum region.

10. The x-ray tube as set forth in claim 9 further including a mechanical bearing means disposed in the lower vacuum region to support the rotor.

11. The x-ray tube as set forth in claim 10 wherein the mechanical bearing is lubricated.

12. The x-ray tube as set forth in claim 8 further including a mechanical bearing disposed in the lower vacuum region to support the rotor.

13. The x-ray tube as set forth in claim 12 wherein the mechanical bearing is lubricated and further including a lubricant vapor condenser for condensing lubricant vapors before the lubricant vapors penetrate the higher vacuum region.

14. The x-ray tube as set forth in claim 7 wherein the means for dividing the toroidal housing interior into higher and lower vacuum regions includes series of interleaved vanes, with some of the vanes being mounted to the rotor and others of the interleaved vanes being mounted to the housing such that the vanes define a sufficiently tortuous path that a vacuum differential is maintained thereacross.

15. The x-ray tube as set forth in claim 14 wherein the vanes are interleaved and define a sufficiently tortuous path that the lower vacuum region is maintained at not more than $10^{-4}$ Torr.

16. The x-ray tube as set forth in claim 14 further including a cooling means for cooling the vanes.

17. The x-ray tube as set forth in claim 16 wherein components which include polymers are disposed in the lower volume region, the vanes being cooled sufficiently to condense polymer vapors.

18. The x-ray tube as set forth in claim 14 further including one of a ball or roller bearing a journal bearing, and a foil bearing disposed in the lower vacuum region.

19. An x-ray tube comprising:

a generally toroidal housing having an evacuated interior;

an annular anode surface mounted in the toroidal housing interior, the anode surface being in thermal communication with a circulated cooling fluid passage such that the cooling fluid removes heat from the anode surface;

an annular rotor rotatably mounted within the housing interior;

at least one cathode assembly mounted to the rotor for rotation therewith, the cathode assembly including a cathode for emitting electrons to form an electron beam that strikes the anode surface to generate an x-ray beam such that the electron beam is rotated around the anode surface as the annular rotor rotates;

an insulating means for electrically insulating the cathode assembly from the rotor such that the cathode assembly is maintainable at a different potential from the rotor;

a means for maintaining the cathode assembly at a potential of at least $-100$ keV relative to the rotor;

an active vacuum pump connected to the housing interior for actively maintaining a vacuum of at least $10^{-6}$ Torr therein.

20. The x-ray tube as set forth in claim 19 further including a means for providing current flow between the rotor and housing to maintain the housing and rotor at substantially a common electrical potential.

21. An x-ray tube comprising:

a generally toroidal housing having an evacuated interior;

an annular anode surface mounted in the toroidal housing interior, the anode surface being in thermal communication with a circulated cooling fluid passage such that the cooling fluid removes heat from the anode surface;

a rotor rotatably disposed within an interior of the toroidal housing;

at least one cathode assembly mounted to the rotor for rotation therewith, the cathode assembly including a means for emitting electrons to form an electron beam that strikes the anode surface to generate an x-ray beam;

an insulating means for electrically insulating the cathode assembly from the rotor;

a means for maintaining the cathode assembly at a high negative potential of at least $-100$ keV relative to the rotor;

a means for transferring a filament current across the vacuum region to the rotor;

an isolation transformer connected between the filament current transferring means and the cathode filament to maintain the cathode filament at the high negative potential relative to the means for transferring the filament current;

an active vacuum pumping means connected to the housing interior for actively maintaining a vacuum of at least $10^{-6}$ Torr therein.

22. The x-ray tube as set forth in claim 21 further including a plurality of cathode assemblies each isolated from the filament current transferring means by an isolation transformer and wherein the means for maintaining the cathode assemblies at the $-100$ keV potential relative to the rotor includes:

an annular electrode connected with the cathode assemblies and extending annularly around and electrically insulated from the rotor, the annular electrode being disposed in close proximity to a hot current filament mounted to the housing, the hot current filament being connected with a high voltage supply means for driving the filament to at least a $-100$ keV potential, electron transfer between the filament and the annular electrode bringing the annular electrode and the cathode filaments to the $-100$ keV potential relative to the housing.

23. An x-ray tube comprising:

a generally toroidal housing having an evacuated interior;

an annular anode surface mounted in the toroidal housing interior, the anode surface being in thermal communication with a circulated cooling fluid passage such that the cooling fluid removes heat from the anode surface;

an annular rotor rotatably disposed within the interior of the toroidal housing;

at least one cathode assembly mounted to the rotor for rotation therewith, the cathode assembly including a cathode that emits electrons to form an electron beam that strikes the anode surface to generate an x-ray beam, the electron beam being rotated around the anode surface as the rotor rotates within the housing interior;

an x-ray beam collimator mounted to the rotor, within the evacuated interior of the housing, and adjacent the cathode assembly for rotation therewith, the collimator including a first pair of collimator walls for defining a thickness of the x-ray beam and a second pair of collimator walls for defining a fan angle of the x-ray beam;

an active vacuum pump connected to the housing interior for actively maintaining a vacuum of at least $10^{-6}$ Torr therein.

24. An x-ray tube comprising:

a generally toroidal housing having an evacuated interior, the housing including a plurality of sections which are clamped together with elastomeric gaskets therebetween for maintaining a vacuum within the housing;

an annular anode surface mounted in the toroidal housing interior, the anode surface being in thermal communication with a circulated cooling fluid passage such that the cooling fluid removes heat from the anode surface;

a rotor rotatably disposed within the housing interior;

at least one cathode mounted to the rotor for rotation therewith, the cathode emitting electrons to form an electron beam that strikes the anode surface to generate an x-ray beam, the electron beam being rotated around the anode surface with the rotor;

an active vacuum pumping means connected to the housing interior for actively maintaining a vacuum of at least $10^{-6}$ Torr therein, the active vacuum pumping means removing outgassing vapors from the elastomeric gaskets.

25. The x-ray tube as set forth in claim 24 wherein the active vacuum pumping means is disposed within the housing and the removable housing sections include an access port for providing access to the active vacuum pumping means.

26. The x-ray tube as set forth in claim 25 wherein the active vacuum pumping means includes an ion pump.

27. The x-ray tube as set forth in claim 25 further including a getter removably disposed within the housing and wherein the removable housing sections include an access port for providing access for replacing the getter.

* * * * *